United States Patent
Moreno

(10) Patent No.: US 7,615,586 B2
(45) Date of Patent: Nov. 10, 2009

(54) COMPOSITION COMPRISING A UREA COMPOUND

(75) Inventor: Angeles Fonolla Moreno, Paris (FR)

(73) Assignee: L'Oreal, Paris (FR)

(*) Notice: Subject to any disclaimer, the term of this patent is extended or adjusted under 35 U.S.C. 154(b) by 534 days.

(21) Appl. No.: 11/266,286

(22) Filed: Nov. 4, 2005

(65) Prior Publication Data
US 2006/0111490 A1    May 25, 2006

Related U.S. Application Data

(60) Provisional application No. 60/645,597, filed on Jan. 24, 2005.

(30) Foreign Application Priority Data

Nov. 9, 2004    (FR)    ................................... 04 52575

(51) Int. Cl.
*C08K 5/00*      (2006.01)
(52) U.S. Cl. .................................................... 524/211
(58) Field of Classification Search .................. 524/211
See application file for complete search history.

(56) References Cited

U.S. PATENT DOCUMENTS

2004/0064026 A1    4/2004    Perrault et al.

FOREIGN PATENT DOCUMENTS

| DE | 27 03 185 | 8/1978 |
|---|---|---|
| EP | 0 816 403 | 1/1998 |
| EP | 1 535 607 | 6/2005 |
| FR | 2 795 083 | 12/2000 |
| WO | WO 01/89591 | 11/2001 |

OTHER PUBLICATIONS

U.S. Appl. No. 11/365,527, filed Mar. 2, 2006, Aubrun-Sonneville.
U.S. Appl. No. 11/365,524, filed Mar. 2, 2006, Aubrun-Sonneville.
U.S. Appl. No. 11/355,164, filed Feb. 16, 2006, Fonolla Moreno, et al.

*Primary Examiner*—Edward J Cain
(74) *Attorney, Agent, or Firm*—Oblon, Spivak, McClelland, Maier & Neustadt, L.L.P.

(57) ABSTRACT

Composition containing, in an aqueous medium, at least one compound of formula (I) described in the specification and its salts, solvates and isomers, and at least one polymer containing at least one monomer having a sulfonic group. The polymer may be in free or partially or totally neutralized form and it may be crosslinked or non-crosslinked. It may be a homopolymer or a copolymer, possibly containing hydrophobic groups. The invention composition is particularly useful in the fields of cosmetics and dermatology, especially for caring for, treating, cleansing and making up the skin and mucous membranes.

25 Claims, No Drawings

COMPOSITION COMPRISING A UREA COMPOUND

REFERENCE TO PRIOR APPLICATIONS

This application claims priority to U.S. provisional application 60/645,597 filed Jan. 24, 2005, and to French patent application 0452575 filed Nov. 9, 2004, both incorporated herein by reference.

FIELD OF THE INVENTION

The invention relates to a composition comprising, in an aqueous medium, a hydroxy urea compound and a polymer comprising at least one monomer comprising a sulfonic group. Preferably, the invention compositon is for topical application, and is especially a cosmetic and/or dermatological composition.

The invention also relates to a process for treating human skin, comprising the application of the composition according to the invention to keratin materials, in particular the skin and/or mucous membranes.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

BACKGROUND OF THE INVENTION

It is known that the skin has a tendency to become dry as a result of environmental factors (pollution, wind, cold, or conditioned air), psychological factors (fatigue or stress) or hormonal factors (menopause). However, it is important for the skin to be well moisturized and not to suffer water loss, which would run the risk of resulting in withered, dried-out skin. Thus, it is common practice to incorporate into cosmetic compositions substances that rehydrate the skin by taking up atmospheric water and by retaining the water in the skin.

Such an improvement in moisturization may be achieved in many ways, and in particular either using active agents that provide water, such as polyols and especially glycerol, or using active agents that protect the skin's hydrolipid film and thus create a barrier effect, which prevents the loss of water from the skin.

Glycerol is a good moisturizer; however, it has the drawback of giving the compositions comprising it a tacky effect that may be unacceptable if the amount of glycerol is too large. To overcome this drawback, it is known practice to combine glycerol with other moisturizers such as urea derivatives. Urea derivatives that are particularly advantageous are hydroxy urea compounds, which do not have the tacky effect of glycerol.

These active agents are incorporated into conventional supports for topical application compositions. The compositions conventionally used in cosmetics and/or dermatology are especially water-in-oil (W/O) emulsions, oil-in-water (O/W) emulsions and aqueous gels. To stabilize and/or thicken these compositions, it is known practice to add gelling polymers thereto. However, the Applicant has observed that hydroxy urea compounds have the drawback of destabilizing compositions comprising the polymers usually used in cosmetics or dermatology, such as carboxyvinyl polymers of the Carbomer type (CTFA name) or carboxyvinyl polymers comprising a hydrophobic group, such as the products sold under the names Pemulen or Carbopol 1342 (CTFA name: Acrylates/C10-30 alkyl acrylate crosspolymer) by the company Noveon.

There is thus still a need for gelled compositions that are stable in the presence of hydroxy urea compounds, especially cosmetic and/or dermatological compositions.

SUMMARY OF THE INVENTION

The inventor has discovered, surprisingly, that compositions comprising a hydroxy urea compound can be stabilized and/or thickened with a polymer comprising a sulfonic function, without any destabilization and/or loss of viscosity taking place.

DETAILED DESCRIPTION OF THE PREFERRED EMBODIMENTS

Thus, one subject of the invention is a composition comprising, in an aqueous medium, (a) at least one compound of formula (I) below:

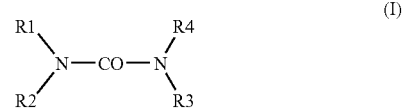

in which:

R1, R2, R3 and R4 represent, independently of each other, a hydrogen atom, a C1-C4 alkyl group or a C2-C6 hydroxyalkyl group comprising from 1 to 5 hydroxyl groups, wherein at least one of the radicals R1 to R4 represents a hydroxyalkyl group, and also the salts, solvates and isomers thereof, and (b) at least one polymer comprising at least one monomer comprising a sulfonic group. The term isomers includes structural isomers, geometric isomers, optical isomers, and stereoisomers.

The composition of the invention has the advantage of not being tacky, while at the same time being stable, i.e. no phase separation, decantation or loss of viscosity takes place.

The term "aqueous medium" means herein a medium comprising water and possibly one or more organic solvents. In addition, since the composition of the invention is preferably a cosmetic and/or dermatological composition, this medium is preferably a physiologically acceptable medium. The term "physiologically acceptable medium" means herein a medium that is compatible with the skin, mucous membranes and the eyes. It is preferably a cosmetically acceptable medium, i.e. a medium that also has an acceptable colour, odour and feel and that does not cause unacceptable discomfort (stinging, tautness or redness) liable to put the consumer off using this composition.

Moreover, the aqueous medium of this composition may comprise a percentage of water of, for example, at least 30% by weight, for example from 30% to 99.8% by weight, preferably from 30% to 90% by weight, better still from 30% to 70% by weight and even better still from 30% to 60% by weight relative to the total weight of the composition.

Advantageously, the pH of the aqueous medium is compatible with keratin materials and especially with the skin. This pH preferably ranges from 3 to 8.5, better still from 3.5 to 7.5, preferentially from 5 to 7 and more preferentially from 5 to 6.

Moreover, in the present patent application, the term "polymer" means either a homopolymer or a copolymer. As indicated below, it may be a crosslinked or non-crosslinked, free or partially or totally neutralized polymer.

The polymer used in the composition according to the invention allows a stable gelled composition to be obtained, which also has good cosmetic properties.

Thus, a subject of the invention is also the use of a polymer comprising at least one monomer comprising a sulfonic group, to gel a cosmetic and/or dermatological composition comprising a compound of formula (I) below:

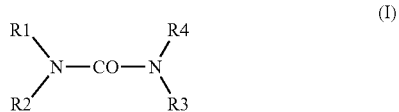

in which:
R1, R2, R3 and R4 represent, independently of each other, a hydrogen atom, a C1-C4 alkyl group or a C2-C6 hydroxyalkyl group comprising from 1 to 5 hydroxyl groups, in which at least one of the radicals R1 to R4 represents a hydroxyalkyl group, and also the salts, solvates and isomers thereof.

Hydroxy Urea Compound

The urea compound present in the composition according to the invention is a compound of formula (I) below:

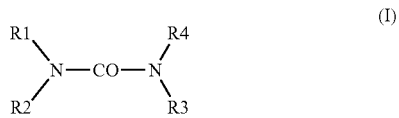

in which:
R1, R2, R3 and R4 represent, independently of each other, a hydrogen atom, a C1-C4 alkyl group or a C2-C6 hydroxyalkyl group comprising from 1 to 5 hydroxyl groups, wherein at least one of the radicals R1 to R4 represents a hydroxyalkyl group, and also the salts, solvates and isomers thereof.

For the compounds of formula (I):
preferably, R1 denotes a C2-C6 hydroxyalkyl group and R2, R3 and R4 denote, independently of each other, a hydrogen atom or a C1-C4 alkyl group;
preferably, R1 denotes a C2-C6 hydroxyalkyl group comprising from 1 to 5 hydroxyl groups and especially 1 hydroxyl group, and R2, R3 and R4 denote a hydrogen atom;
more preferentially, R1 denotes a C2-C4 hydroxyalkyl group comprising one hydroxyl group and R2, R3 and R4 denote a hydrogen atom.

C1-C4 alkyl groups that may especially be mentioned include methyl, ethyl, n-propyl, isopropyl, n-butyl, isobutyl and tert-butyl groups.

Among the C1-C6 hydroxyalkyl groups that are preferred are those comprising only one hydroxyl group and in particular hydroxyethyl, hydroxypropyl, hydroxybutyl, hydroxypentyl and hydroxyhexyl groups.

Salts of such compounds that may be mentioned include the salts of mineral acids, such as sulfuric acid, hydrochloric acid, hydrobromic acid, hydriodic acid, phosphoric acid and boric acid. Mention may also be made of the salts of organic acids, which may comprise one or more carboxylic acid, sulfonic acid or phosphonic acid groups. They may be linear, branched or cyclic aliphatic acids or alternatively aromatic acids. These acids may also comprise one or more hetero atoms chosen from O and N, for example in the form of hydroxyl groups. Mention may especially be made of propionic acid, acetic acid, terephthalic acid, citric acid and tartaric acid.

The term "solvate" means a stoichiometric mixture of the compound of formula (I) with one or more water molecules or organic solvent molecules, such as a mixture derived from the synthesis of the compound of formula (I).

Preferred compounds of formula (I) that may be mentioned include N-(2-hydroxyethyl)urea; N-(2-hydroxypropyl)urea; N-(3-hydroxypropyl)urea; N-(2,3-dihydroxypropyl)urea; N-(2,3,4,5,6-pentahydroxyhexyl)urea; N-methyl-N-(1,3,4,5, 6-pentahydroxy-2-hexyl)urea; N-methyl-N'-(1-hydroxy-2-methyl-2-propyl)urea; N-(1-hydroxy-2-methyl-2-propyl) urea; N-(1,3-dihydroxy-2-propyl)urea; N-[tris (hydroxymethyl)-methyl]urea; N-ethyl-N'-(2-hydroxyethyl) urea; N,N-bis(2-hydroxyethyl)urea; N,N'-bis(2-hydroxyethyl)-urea; N,N-bis(2-hydroxypropyl)urea; N,N'-bis(2-hydroxypropyl)urea; N,N-bis(2-hydroxyethyl)-N'-propylurea; N,N-bis(2-hydroxypropyl)-N'-(2-hydroxyethyl) urea; N-tert-butyl-N'-(2-hydroxyethyl)-N'-(2-hydroxypropyl)urea; N-(1,3-dihydroxy-2-propyl)-N'-(2-hydroxyethyl)urea; N,N-bis(2-hydroxyethyl)-N', N'-dimethylurea; N,N,N'N'-tetrakis(2-hydroxyethyl)urea; N'N'-bis(2-hydroxyethyl)-N',N'-bis(2-hydroxypropyl)urea; and mixtures thereof.

Preferably, the compound of formula (I) is N-(2-hydroxyethyl)urea.

The compounds of formula (I) are known compounds and are described especially in patent application DE-A-2 703 185. Among these, N-(2-hydroxyethyl)urea is also commercially available, in the form of a mixture set at 50% by weight in water, from the company National Starch under the trade name Hydrovance®.

The compound of formula (I) may be present in the composition according to the invention in any amount, and preferably in a content ranging from 0.1% to 50% by weight, more preferably ranging from 0.1% to 20% by weight and preferentially ranging from 0.1% to 10% by weight relative to the total weight of the composition.

Polymer Comprising at Least One Monomer Comprising a Sulfonic Group

The polymers comprising at least one monomer comprising a sulfonic group, which are used in the composition of the invention, are water-soluble or water-dispersible or swellable in water. The polymers used in accordance with the invention may be homopolymers or copolymers and may be obtained from at least one ethylenically unsaturated monomer comprising a sulfonic group, which may be in free or partially or totally neutralized form. These polymers may optionally comprise at least one hydrophobic group and may then constitute an amphiphilic polymer (or hydrophobic modified polymer).

Preferentially, the polymers in accordance with the invention may be partially or totally neutralized with a mineral base (e.g., sodium hydroxide, potassium hydroxide or aqueous ammonia) or an organic base such as monoethanolamine, diethanolamine, triethanolamine, an aminomethylpropanediol, N-methylglucamine, basic amino acids, for instance arginine and lysine, and mixtures of these compounds. They are generally neutralized. In the present invention, the term "neutralized" means polymers that have been totally or almost totally neutralized, i.e. at least 90% neutralized.

The polymers used in the composition of the invention generally have, but are not required to have, a number-average molecular weight ranging from 1000 to 20 000 000 g/mol, preferably ranging from 20 000 to 5 000 000 and even more preferentially from 100 000 to 1 500 000 g/mol.

These polymers according to the invention may be crosslinked or non-crosslinked.

The monomers comprising a sulfonic group in the polymer used in the composition of the invention include those chosen especially from vinylsulfonic acid, styrenesulfonic acid, (meth)acrylamido($C_1$-$C_{22}$)alkylsulfonic acids, N-($C_1$-$C_{22}$) alkyl(meth)acrylamido($C_1$-$C_{22}$)alkylsulfonic acids, for instance undecylacrylamidomethanesulfonic acid, and also the partially or totally neutralized forms thereof, and mixtures thereof.

According to one preferred embodiment of the invention, the monomers comprising a sulfonic group are chosen from (meth)acrylamido($C_1$-$C_{22}$)alkylsulfonic acids, for instance acrylamidomethanesulfonic acid, acrylamidoethanesulfonic acid, acrylamidopropanesulfonic acid, 2-acrylamido-2-methylpropanesulfonic acid, 2-methacrylamido-2-methylpropanesulfonic acid, 2-acrylamido-n-butanesulfonic acid, 2-acrylamido-2,4,4-trimethylpentanesulfonic acid, 2-methacrylamido-dodecylsulfonic acid or 2-acrylamido-2,6-dimethyl-3-heptanesulfonic acid, and also the partially or totally neutralized forms thereof, and mixtures thereof.

More particularly, 2-acrylamido-2-methylpropanesulfonic acid (AMPS) and partially or totally neutralized forms thereof are used.

When the polymers are crosslinked, the crosslinking agents are not limited, and may be chosen for example from the polyolefinically unsaturated compounds commonly used for crosslinking the polymers obtained by free-radical polymerization.

Examples of crosslinking agents that may be mentioned include divinylbenzene, diallyl ether, dipropylene glycol diallyl ether, polyglycol diallyl ethers, triethylene glycol divinyl ether, hydroquinone diallyl ether, ethylene glycol or tetraethylene glycol di(meth)acrylate, trimethylolpropane triacrylate, methylenebisacrylamide, methylenebismethacrylamide, triallylamine, triallyl cyanurate, diallyl maleate, tetraallylethylenediamine, tetraallyloxyethane, trimethylolpropane diallyl ether, allyl (meth) acrylate, allylic ethers of alcohols of the sugar series, or other allylic or vinyl ethers of polyfunctional alcohols, and also the allylic esters of phosphoric and/or vinylphosphonic acid derivatives, or mixtures of these compounds.

According to one preferred embodiment of the invention, the crosslinking agent is chosen from methylenebisacrylamide, allyl methacrylate and trimethylolpropane triacrylate (TMPTA). The degree of crosslinking is not limited, but generally ranges from 0.01 mol % to 10 mol % and more particularly from 0.2 mol % to 2 mol % relative to the polymer.

When the polymers used are homopolymers, they comprise only monomers comprising a sulfonic group and, if they are crosslinked, one or more crosslinking agents. Copolymers according to the invention comprise at least one type of monomer comprising a sulfonic group according to the invention, or two or more thereof, and in addition may further comprise other monomers. If they are crosslinked, they also comprise one or more crosslinking agents.

The homopolymers of the invention are generally preferably crosslinked and neutralized, and they may be obtained according to the preparation process comprising the following steps:

(a) the monomer such as 2-acrylamido-2-methylpropane-sulfonic acid in free form as dispersed or dissolved in a solution of tert-butanol or of water and tert-butanol;
(b) the monomer solution or dispersion obtained in (a) is neutralized with one or more mineral or organic bases, preferably aqueous ammonia $NH_3$, in an amount making it possible to obtain a degree of neutralization of the sulfonic acid functions of the polymer ranging from 90% to 100%;
(c) the crosslinking monomer(s) is(are) added to the solution or dispersion obtained in (b);
(d) a standard free-radical polymerization is performed in the presence of free-radical initiators at a temperature ranging from 10 to 150° C.; the polymer precipitates in the tert-butanol-based solution or dispersion.

The preferred AMPS homopolymers generally contain, randomly distributed:
a) from 90% to 99.9% by weight of units of general formula (II) below:

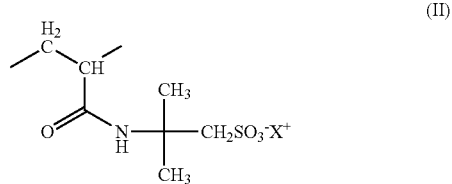

in which $X^+$ denotes a proton, an alkali metal cation, an alkaline-earth metal cation or an ammonium ion, not more than 10 mol % of the cations $X^+$ possibly being protons $H^+$;
b) from 0.01% to 10% by weight of crosslinking units derived from at least one monomer comprising at least two olefinic double bonds; the weight proportions are defined relative to the total weight of the polymer.

The homopolymers according to the invention that are more particularly preferred comprise from 98% to 99.5% by weight of units of formula (II) and from 0.2% to 2% by weight of crosslinking units.

A polymer of this type that may especially be mentioned is the crosslinked and neutralized homopolymer of 2-acrylamido-2-methylpropanesulfonic acid sold by the company Clariant under the trade name "Hostacerin AMPS" (CTFA name: Ammonium polyacryl-dimethyltauramide).

The polymer may also be an amphiphilic homopolymer (or hydrophobic modified homopolymer) chosen from random amphiphilic polymers of AMPS modified by reaction with a $C_6$-$C_{22}$ mono-n-alkylamine or di-n-alkylamine, such as those described in document WO-A-00/31154, which are grafted homopolymers.

When the polymers used are copolymers, they may be obtained from ethylenically unsaturated monomers comprising a sulfonic group according to the invention and from other ethylenically unsaturated monomers, i.e. from ethylenically unsaturated monomers not comprising a sulfonic group. However, included herein are copolymers containing more than one type of invention monomer comprising a sulfonic group, and no other type of monomer.

Preferably, the ethylenically unsaturated monomers comprising a sulfonic group are chosen from those described above.

The ethylenically unsaturated monomers not comprising a sulfonic group include those chosen from ethylenically unsaturated hydrophilic monomers and ethylenically unsaturated hydrophobic monomers, and mixtures thereof. When the polymer comprises hydrophobic monomers, it constitutes an amphiphilic polymer (also known as a hydrophobic modified polymer).

The ethylenically unsaturated hydrophilic monomers may be chosen, for example, from (meth)acrylic acids, the β-substituted alkyl derivatives thereof or the esters thereof obtained with monoalcohols or monoalkylene or polyalkylene glycols, (meth)acrylamides, vinylpyrrolidone, vinylformamide, maleic anhydride, itaconic acid and maleic acid, or mixtures of these compounds.

When the polymer of the composition according to the invention is a copolymer that may be obtained from ethylenically unsaturated monomers comprising a sulfonic group and from ethylenically unsaturated hydrophilic monomers, it may be chosen especially from (1) crosslinked anionic copolymers of acrylamide or methacrylamide and of 2-acrylamido-2-methylpropanesulfonic acid, especially those in the form of a W/O emulsion, such as those sold under the name Sepigel 305 by the company SEPPIC (CTFA name: Polyacrylamide/C13-14 Isoparaffin/Laureth-7), under the name Simulgel 600 by the company SEPPIC (CTFA name: Acrylamide/Sodium acryloyldimethyltaurate copolymer/Isohexadecane/Polysorbate 80), (2) copolymers of (meth)acrylic acid or of (meth)acrylate and of 2-acrylamido-2-methylpropanesulfonic acid, especially those in the form of a W/O emulsion, such as those sold under the name Simulgel NS by the company SEPPIC (copolymer of sodium acrylamido-2-methylpropane-sulfonate/hydroxyethyl acrylate as a 40% inverse emulsion in Polysorbate 60 and squalane) (CTFA name: Hydroxyethyl acrylate/Sodium acryloyldimethyltaurate copolymer/Squalane/Polysorbate 60), or those sold under the name Simulgel EG by the company SEPPIC (copolymer of acrylic acid/acrylamido-2-methylpropanesulfonic acid in the form of the sodium salt, as a 45% inverse emulsion in isohexadecane/water) (CTFA name: Sodium acrylate/Sodium acryloyldimethyltaurate copolymer/Isohexadecane/Polysorbate 80), and (3) copolymers of 2-acrylamido-2-methylpropanesulfonic acid and of vinylpyrrolidone or of vinylformamide, such as the products sold under the name Aristoflex AVC by the company Clariant.

When the monomers comprising a sulfonic group are copolymerized with ethylenically unsaturated hydrophobic monomers comprising a hydrophobic chain, also known as a fatty chain (e.g., C6-C50 chain), the polymer obtained is amphiphilic, i.e. it comprises both a hydrophilic portion and a hydrophobic portion. Such polymers are also known as hydrophobic modified polymers.

These hydrophobic modified polymers may also comprise one or more monomers comprising neither a sulfonic group nor a fatty chain, such as (meth)acrylic acids, β-substituted alkyl derivatives thereof or esters thereof obtained with monoalcohols or with monoalkylene or polyalkylene glycols, (meth)acrylamides, vinylpyrrolidone, vinylformamide, maleic anhydride, itaconic acid or maleic acid, or mixtures of these compounds.

Hydrophobic modified polymers that may especially be used include those that may be obtained from 2-acrylamido-2-methylpropanesulfonic acid (AMPS) and from at least one ethylenically unsaturated hydrophobic monomer comprising at least one group comprising from 6 to 50 carbon atoms, more preferentially from 6 to 22 carbon atoms, even more preferentially from 6 to 18 carbon atoms and more particularly 12 to 18 carbon atoms.

These polymers are described especially in documents EP-A-750 899, U.S. Pat. No. 5,089,578 and WO-A-2004/43689, and in the following publications by Yotaro Morishima:

"Self-assembling amphiphilic polyelectrolytes and their nanostructures—Chinese Journal of Polymer Science Vol. 18, No. 40, (2000), 323-336";

"Micelle formation of random copolymers of sodium 2-(acrylamido)-2-methylpropanesulfonate and a nonionic surfactant macromonomer in water as studied by fluorescence and dynamic light scattering—Macromolecules 2000, Vol. 33, No. 10-3694-3704";

"Solution properties of micelle networks formed by nonionic moieties covalently bound to a polyelectrolyte: salt effects on rheological behaviour Langmuir, 2000, Vol. 16, No. 12, 5324-5332"; "Stimuli responsive amphiphilic copolymers of sodium 2-(acrylamido)-2-methylpropanesulfonate and associative macromonomers—Polym. Preprint, Div. Polym. Chem. 1999, 40(2), 220-221"

The hydrophobic monomers of these particular polymers are preferably chosen from the acrylates, alkylacrylates, acrylamides or alkylacrylamides of formula (III) below:

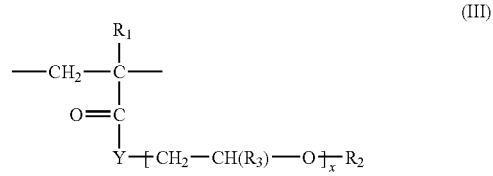

(III)

in which $R_1$ and $R_3$, which may be identical or different, denote a hydrogen atom or a substantially linear or branched $C_1$-$C_6$ alkyl radical (preferably methyl); Y denotes O or NH; $R_2$ denotes a hydrocarbon-based radical comprising from 6 to 50 carbon atoms, more preferentially from 6 to 22 carbon atoms, even more preferentially from 6 to 18 carbon atoms and more particularly from 12 to 18 carbon atoms; x denotes a number of moles of alkylene oxide and ranges from 0 to 100.

The radical $R_2$ is preferably chosen from $C_6$-$C_{18}$ alkyl radicals that are substantially linear (for example n-hexyl, n-octyl, n-decyl, n-hexadecyl, n-dodecyl or lauryl, and n-octadecyl or stearyl), branched or cyclic (for example cyclododecane ($C_{12}$) or adamantane ($C_{10}$)); $C_6$-$C_{18}$ perfluoroalkyl radicals (for example the group of formula—$(CH_2)_2$—$(CF_2)_9$—$CF_3$); the cholesteryl radical ($C_{27}$) or a cholesterol ester residue, for instance the cholesteryl oxyhexanoate group; aromatic polycyclic groups, for instance naphthalene or pyrene. Among these radicals, substantially linear alkyl radicals, and more particularly the n-dodecyl, n-hexadecyl or n-octadecyl radical, and mixtures thereof, are more particularly preferred.

According to one particularly preferred form of the invention, the monomer of formula (III) comprises at least one alkylene oxide unit (x≧1) and preferably several alkylene oxide units (x>1) constituting a polyoxyalkylene chain. The polyoxyalkylene chain preferably consists of ethylene oxide units and/or propylene oxide units and even more particularly consists of ethylene oxide units. The number of oxyalkylene units (or number of moles of alkylene oxide) generally ranges from 3 to 100, more preferentially from 3 to 50 and even more preferentially from 7 to 25.

Among these polymers, mention may be made of:

crosslinked or non-crosslinked, neutralized or non-neutralized copolymers, comprising from 15% to 60% by weight of AMPS units and from 40% to 85% by weight of ($C_8$-$C_{16}$)alkyl (meth)acrylamide units or of ($C_8$-$C_{16}$) alkyl meth(acrylate) units relative to the polymer, such as those described in document EP-A-750 899;

terpolymers comprising from 10 mol % to 90 mol % of acrylamide units, from 0.1 mol % to 10 mol % of AMPS units and from 5 mol % to 80 mol % of n-($C_6$-$C_{18}$)alkylacrylamide units, relative to the polymer, such as those described in document U.S. Pat. No. 5,089,578, non-crosslinked copolymers of partially or totally neutralized AMPS and of n-dodecyl, n-hexadecyl or n-octadecyl methacrylate, such as those described in the Morishima articles cited above;

crosslinked or non-crosslinked copolymers of partially or totally neutralized AMPS and of n-dodecylmethacrylamide, such as those described in the Morishima articles cited above.

Hydrophobic modified polymers that may be mentioned more particularly include copolymers consisting (i) of 2-acrylamido-2-methylpropanesulfonic acid (AMPS) units of formula (II) indicated above, in which $X^+$ is a proton, an alkali metal cation, an alkaline-earth metal cation or an ammonium ion, and (ii) of units of formula (IV) below:

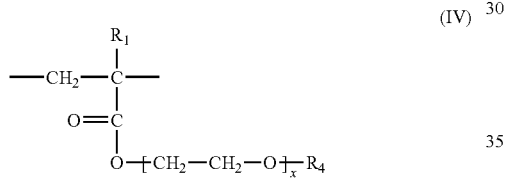

(IV)

in which x denotes an integer ranging from 3 to 100, preferably from 3 to 50 and more preferentially from 7 to 25; $R_1$ has the same meaning as that indicated above in formula (III) and $R_4$ denotes a linear or branched alkyl radical comprising from 6 to 22 carbon atoms and preferably from 10 to 22 carbon atoms.

The hydrophobic modified polymers of this type are especially those described in the Morishima articles cited above, for which x=25, $R_1$ denotes methyl and $R_4$ represents n-dodecyl; or those described in document WO-A-02/43689, for which x=8 or 25, $R_1$ denotes methyl and $R_4$ represents n-hexadecyl ($C_{16}$), n-octadecyl ($C_{18}$) or n-dodecyl ($C_{12}$), or mixtures thereof. The polymers for which $X^+$ denotes sodium or ammonium are more particularly preferred.

The preferred hydrophobic modified polymers that may be used in the composition in accordance with the invention may be obtained according to the standard free-radical polymerization processes in the presence of one or more initiators, for instance azobisisobutyronitrile (AIBN), azobisdimethylvaleronitrile, 2,2-azobis[2-amidinopropane] hydrochloride (ABAH=2,2-azobis[2-amidinopropane] hydrochloride), organic peroxides such as dilauryl peroxide, benzoyl peroxide, tert-butyl hydroperoxide, etc., mineral peroxide compounds such as potassium persulfate or ammonium persulfate, or $H_2O_2$ optionally in the presence of reducing agents.

These hydrophobic modified polymers may especially be obtained by free-radical polymerization in tert-butanol medium, from which they precipitate. By using polymerization by precipitation in tert-butanol, it is possible to obtain a size distribution of the polymer particles that is particularly favourable for its uses.

The reaction may be performed at a temperature of between 0 and 150° C. and preferably between 10 and 100° C., either at atmospheric pressure or under reduced pressure. It may also be performed under an inert atmosphere and preferably under nitrogen.

These preferred hydrophobic modified polymers are, in particular, those described in document EP-1 069 142, and especially those obtained by polymerization of 2-acrylamido-2-methylpropanesulfonic acid (AMPS) or a sodium or ammonium salt thereof, with a (meth)acrylic acid ester and of a $C_{10}$-$C_{18}$ alcohol oxyethylenated with 8 mol of ethylene oxide (Genapol® C-080 from the company Clariant), of a $C_{11}$ oxo alcohol oxyethylenated with 8 mol of ethylene oxide (Genapol® UD-080 from the company Clariant), of a $C_{11}$ oxo alcohol oxyethylenated with 7 mol of ethylene oxide (Genapol® UD-070 from the company Clariant), of a $C_{12}$-$C_{14}$ alcohol oxyethylenated with 7 mol of ethylene oxide (Genapol® LA-070 from the company Clariant), of a $C_{12}$-$C_{14}$ alcohol oxyethylenated with 9 mol of ethylene oxide (Genapol® LA-090 from the company Clariant), of a $C_{12}$-$C_{14}$ alcohol oxyethylenated with 11 mol of ethylene oxide (Genapol® LA-110 from the company Clariant), of a $C_{16}$-$C_{18}$ alcohol oxyethylenated with 8 mol of ethylene oxide (Genapol® T-080 from the company Clariant), of a $C_{16}$-$C_{18}$ alcohol oxyethylenated with 15 mol of ethylene oxide (Genapol® T-150 from the company Clariant), of a $C_{16}$-$C_{18}$ alcohol oxyethylenated with 11 mol of ethylene oxide (Genapol® T-110 from the company Clariant), of a $C_{16}$-$C_{18}$ alcohol oxyethylenated with 20 mol of ethylene oxide (Genapol® T-200 from the company Clariant), of a $C_{16}$-$C_{18}$ alcohol oxyethylenated with 25 mol of ethylene oxide (Genapol® T-250 from the company Clariant), of a $C_{18}$-$C_{22}$ alcohol oxyethylenated with 25 mol of ethylene oxide and/or of an iso-$C_{16}$-$C_{18}$ alcohol oxyethylenated with 25 mol of ethylene oxide.

The molar percentage concentration of the units of formula (II) and of the units of formula (IV) in the polymers according to the invention may vary as a function of the intended (cosmetic) application and of the desired rheological properties of the formulation. It may range for example between 0.1 mol % and 99.9 mol %.

Preferably, for the polymers that are the most hydrophobic, the molar proportion of units for formula (II) or (IV) ranges from 50.1% to 99.9%, more particularly from 70% to 95% and even more particularly from 80% by 90%.

Preferably, for the sparingly hydrophobic polymers, the molar proportion of units of formula (II) or (IV) ranges from 0.1% to 50%, more particularly from 5% to 25% and even more particularly from 10% to 20%.

The monomer distribution in the polymers of the invention may be, for example, alternate, block (including multiblock) or random.

As hydrophobic modified polymers of this type, mention may be made especially of the copolymer of AMPS and of ethoxylated C12-C14 alkyl methacrylate (non-crosslinked copolymer obtained from Genapol LA-070 and from AMPS) (CTFA name: Ammonium Acryloyldimethyltaurate/Laureth-7 Methacrylate Copolymer) sold under the name Aristoflex LNC by the company Clariant, and the copolymer of AMPS and of ethoxylated (25 EO) stearyl methacrylate (copolymer crosslinked with trimethylolpropane triacrylate, obtained from Genapol T-250 and AMPS) (CTFA name: Ammonium Acryloyldimethyltaurate/Steareth-25 Methacrylate Crosspolymer) sold under the name Aristoflex HMS by the company Clariant.

The polymer(s) comprising at least one monomer comprising a sulfonic group, which are used in the composition in accordance with the invention, are preferably present in active material amounts ranging, for example, from 0.01% to 20% by weight, preferably from 0.1% to 10% by weight, preferentially from 0.1% to 5% by weight and even more preferentially from 0.5% to 2% by weight relative to the total weight of the composition.

Additives

In addition to water, the medium of the composition of the invention may comprise one or more organic solvents that may be chosen from the group consisting of hydrophilic organic solvents, lipophilic organic solvents and amphiphilic solvents, or mixtures thereof.

Included among the hydrophilic organic solvents that may be mentioned, for example, are linear or branched monohydric alcohols comprising from 1 to 8 carbon atoms, for instance ethanol, propanol, butanol, isopropanol and isobutanol; polyethylene glycols comprising from 6 to 80 ethylene oxides; polyols such as propylene glycol, isoprene glycol, butylene glycol, glycerol and sorbitol; mono- or dialkyl isosorbides in which the alkyl groups comprise from 1 to 5 carbon atoms, for instance dimethyl isosorbide; glycol ethers, for instance diethylene glycol monomethyl or monoethyl ether and propylene glycol ethers, for instance dipropylene glycol methyl ether.

Amphiphilic organic solvents that may be mentioned include polypropylene glycol (PPG) derivatives such as fatty acid esters of polypropylene glycol, fatty alkyl ethers of PPG, for instance PPG-23 oleyl ether, and PPG-36 oleate.

Lipophilic organic solvents that may be mentioned, for example, include fatty esters such as diisopropyl adipate, dioctyl adipate and alkyl benzoates.

According to the desired aim, the compositions according to the present invention may comprise only an aqueous medium (water and hydrophilic solvents and additives) or they may also comprise lipophilic constituents such as fatty substances, for instance oils and lipophilic additives.

Thus, the compositions according to the present invention may be in any form, including those that are suitable for topical application, especially in the form of aqueous gels, in the form of emulsions obtained by dispersing a fatty phase (also known as an oily phase) in an aqueous phase (O/W) or, conversely, (W/O) or multiple emulsions (for example W/O/W, O/W/O or O/O/W). They may be more or less fluid and may have the appearance of a white or coloured cream, a pomade, a milk, a lotion, a serum or a paste. These compositions are prepared according to the usual methods.

According to one particular embodiment of the invention, the composition according to the present invention is in the form of an emulsion and in this case comprises at least one oily phase. The proportion of the aqueous phase may range for example from 20% to 99%, preferably from 50% to 98% and better still from 60% to 98% by weight relative to the total weight of the composition.

The proportion of the oily phase of the emulsion may range for example from 1% to 80% by weight, preferably from 2% to 50% by weight and better still from 2% to 40% by weight relative to the total weight of the composition. The fatty substances of the oily phase, especially the oils, and the emulsifiers and co-emulsifiers that may be present, used in the composition in emulsion form are chosen from those conventionally used in cosmetics or dermatology. The emulsifier and the co-emulsifier, when they are present, are generally in a proportion ranging from 0.1% to 30% by weight, preferably from 0.3% to 20% by weight and better still from 0.5% to 15% by weight relative to the total weight of the composition. The emulsion may also comprise lipid vesicles in addition to or instead of the emulsifiers and/or co-emulsifiers.

The emulsions generally comprise at least one emulsifier chosen from amphoteric, anionic, cationic and nonionic emulsifiers, used alone or as a mixture. The emulsifiers are chosen in an appropriate manner according to the continuous phase of the emulsion to be obtained (W/O or O/W). When the emulsion is multiple, it generally comprises an emulsifier in the primary emulsion and an emulsifier in the outer phase into which the primary emulsion is introduced.

As emulsifiers that may be used for the preparation of the W/O emulsions, examples that may be mentioned include alkyl esters or ethers of sorbitan, of glycerol or of sugars; silicone surfactants, for instance dimethicone copolyols such as the mixture of cyclomethicone and of dimethicone copolyol, sold under the names DC 5225 C and DC 3225 C by the company Dow Corning, and alkyldimethicone copolyols such as laurylmethicone copolyol sold under the name "Dow Corning 5200 Formulation Aid" by the company Dow Corning, cetyl dimethicone copolyol sold under the name Abil EM 90® by the company Goldschmidt, and the mixture of Polyglyceryl-4 isostearate/cetyl dimethicone copolyol/hexyl laurate sold under the name Abil WE 09® by the company Goldschmidt. One or more co-emulsifiers may also be added thereto, which may be chosen, advantageously, from the group comprising branched-chain fatty acid esters of polyol, and especially branched-chain fatty acid esters of glycerol and/or of sorbitan, for example polyglyceryl isostearate, such as the product sold under the name Isolan GI 34 by the company Goldschmidt, sorbitan isostearate, such as the product sold under the name Arlacel 987 by the company ICI, sorbitan glyceryl isostearate, such as the product sold under the name Arlacel 986 by the company ICI, and mixtures thereof.

As emulsifiers that may be used for the preparation of the O/W emulsions, examples that may be mentioned include nonionic emulsifiers such as fatty acid esters of oxyalkylenated (more particularly polyoxyethylenated) polyols, for example polyethylene glycol stearates, for instance PEG-100 stearate, PEG-50 stearate and PEG-40 stearate; fatty acid esters of oxyalkylenated sorbitan comprising, for example, from 20 to 100 EO, for example those sold under the trade names Tween 20 or Tween 60 by the company Uniqema; oxyalkylenated (oxyethylenated and/or oxypropylenated) fatty alkyl ethers; alkoxylated or non-alkoxylated sugar esters, for instance sucrose stearate such as PEG-20 methylglucose sesquistearate; sorbitan esters such as the sorbitan palmitate sold under the name Span 40 by the company Uniqema; diacid esters of fatty alcohols, for instance dimyristyl tartrate; mixtures of these emulsifiers, for instance the mixture of glyceryl stearate and of PEG-100 stearate (CTFA name: Glyceryl Stearate/PEG-100 Stearate) sold under the name Arlacel 165 by the company Uniqema and under the name Simulsol 165 by the company SEPPIC; or the mixture of dimyristyl tartrate, cetearyl alcohol, Pareth-7 and PEG-25 laureth-25, sold under the name Cosmacol PSE by the company Sasol (CTFA name: Dimyristyl tartrate/cetearyl alcohol/12-15 Pareth 7/PPG 25 laureth 25).

Co-emulsifiers such as, for example, fatty alcohols comprising from 8 to 26 carbon atoms, for instance cetyl alcohol, stearyl alcohol and the mixture thereof (cetearyl alcohol), octyldodecanol, 2-butyloctanol, 2-hexyldecanol, 2-undecylpentadecanol or oleyl alcohol, or fatty acids, may be added to these emulsifiers.

It is also possible to prepare emulsions without emulsifying surfactants or comprising less than 0.5% of them relative to the total weight of the composition, by using suitable compounds, for example the amphiphilic polymers indicated above as polymers that may be used according to the invention.

When the composition of the invention is in emulsion form, it comprises at least one oily phase that comprises at least one oil, especially a cosmetic oil. The term "oil" means a fatty substance that is liquid at room temperature (25° C.).

As oils that may be used in the composition of the invention, it is possible to use, for example, hydrocarbon-based oils of animal origin, such as perhydrosqualene (or squalane); hydrocarbon-based oils of plant origin, such as caprylic/capric acid triglycerides, for instance those sold by the company Stearineries Dubois or those sold under the names Miglyol 810, 812 and 818 by the company Dynamit Nobel, or alternatively oils of plant origin, for instance sunflower oil, corn oil, soybean oil, marrow oil, grapeseed oil, sesame seed oil, hazelnut oil, apricot oil, macadamia oil, arara oil, coriander oil, castor oil, avocado oil, jojoba oil and shea butter oil; synthetic oils; silicone oils, for instance volatile or non-volatile polymethylsiloxanes (PDMS) comprising a linear or cyclic silicone chain, which are liquid or pasty at room temperature; fluoro oils, such as partially hydrocarbon-based and/or silicone-based fluoro oils, for instance those described in document JP-A-2 295 912; ethers, such as dicaprylyl ether (CTFA name: Dicaprylyl ether); and $C_{12}$-$C_{15}$ fatty alkyl benzoates (Finsolv TN from Finetex); mixtures thereof.

The oily phase may also comprise one or more fatty substances chosen, for example, from fatty alcohols (cetyl alcohol, stearyl alcohol or cetearyl alcohol), fatty acids (stearic acid) or waxes (paraffin, polyethylene wax, carnauba wax or beeswax).

The composition according to the invention may comprise any additive such as those usually used in cosmetic or dermatological compositions, for instance preserving agents, fillers, pH regulators (acids or bases), or sunscreens. Needless to say, a person skilled in the art will take care to select the optional compound(s) to be added to the composition according to the invention such that the advantageous properties intrinsically associated with the composition in accordance with the invention are not, or are not substantially, adversely affected by the envisaged addition.

As fillers that may be used in the composition of the invention, examples that may be mentioned include pigments; silica powder; talc; polyamide particles and especially those sold under the name Orgasol by the company Atochem; polyethylene powders; powders of natural organic materials such as starch powders, especially of crosslinked or non-crosslinked corn starch, wheat starch or rice starch, such as the starch powders crosslinked with octenylsuccinate anhydride sold under the name Dry-Flo by the company National Starch; microspheres based on acrylic copolymers, such as those made of ethylene glycol dimethacrylate/lauryl methacrylate copolymer sold by the company Dow Corning under the name Polytrap; polymethyl methacrylate powders such as those sold under the name Micropearl M 100 by the company Matsumoto; expanded powders such as hollow microspheres and especially the microspheres sold under the name Expancel by the company Kemanord Plast or under the name Micropearl F 80 ED by the company Matsumoto; silicone resin microbeads such as those sold under the name Tospearl by the company Toshiba Silicone; polyurethane powders such as the hexamethylene diisocyanate/trimethylol hexyl lactone copolymer powder sold under the name Plastic Powder D-400 by the company Toshiba Pigment (CTFA name: HDI/Trimethylol Hexyllactone Crosspolymer); and mixtures thereof. When they are present, these fillers may be in amounts ranging from 0.001% to 20% by weight, preferably from 0.1% to 10% by weight and better still from 1% to 5% by weight relative to the total weight of the composition.

The composition according to the invention may constitute a skincare product, especially for the face, the neck, around the eyes or the body; or alternatively a skin makeup product such as a complexion product (especially a foundation), an eyeshadow, a makeup rouge, an eyeliner, a concealer product or a body makeup product; or alternatively an antisun product with incorporated screening agents; or alternatively a skin cleansing product.

In a preferred embodiment the composition is generally not rinsed out, but it may be rinsed out for example if it is a cleansing product and especially a foaming product.

A subject of the invention is also a cosmetic process for treating a keratin material such as the skin, the eyelashes, the eyebrows, the nails or mucous membranes, wherein a composition as defined above is applied to the keratin material.

A subject of the invention is also the use of the composition as defined above for preparing a pomade or an ointment for the therapeutic treatment of the human face and/or body.

Packaging:

According to another aspect, the invention also relates to a cosmetic assembly comprising:
  i) a container delimiting at least one compartment, the container being closed by a closing member; and
  ii) a composition as described above, preferably in a more solid form such as a cream, placed inside the compartment.

The container may be in any adequate form. It may especially be in the form of a bottle, a tube, a jar, a case, a box, a sachet or a carton.

The closing member may be, for example, in the form of a removable stopper, a lid, a cap, a tear-off strip or a capsule, especially of the type comprising a body attached to the container and a cover cap articulated on the body. It may also be in the form of a member for selectively closing the container, especially a pump, a valve or a flap valve.

The container may be combined with an applicator, especially in the form of a brush comprising an arrangement of bristles maintained by a twisted wire. Such a twisted brush is described especially in U.S. Pat. No. 4,887,622. It may also be in the form of a comb comprising a plurality of application members, obtained especially by moulding. Such combs are described, for example, in patent FR 2 796 529. The applicator may be in the form of a fine brush, as described, for example, in patent FR 2 722 380. The applicator may be in the form of a block of foam or of elastomer, a felt or a spatula. The applicator may be free (tuft or sponge) or securely fastened to a rod borne by the closing member, as described, for example, in U.S. Pat. No. 5,492,426. The applicator may be securely fastened to the container, as described, for example, in patent FR 2 761 959.

The product may be placed directly in the container, or indirectly. By way of example, the product may be arranged on an impregnated support, especially in the form of a wipe or a pad, and arranged (individually or in plurality) in a box or in a sachet. Such a support incorporating a product is described, for example, in patent application WO 01/03538.

The closing member may be coupled to the container by screwing. Alternatively, the coupling between the closing member and the container is done other than by screwing, especially via a bayonet mechanism, by click-fastening, gripping, welding, bonding or by magnetic attraction. The term "click-fastening" in particular means any system involving the crossing of a bead or cord of material by elastic deformation of a portion, especially of the closing member, followed by return to the elastically unconstrained position of the portion after the crossing of the bead or cord.

The container may be at least partially made of thermoplastic material. Examples of thermoplastic materials that may be mentioned include polypropylene or polyethylene.

to which it may be securely fastened. Such a drainer is described, for example in patent FR 2 792 618.

The content of the patents or patent applications mentioned above is incorporated by reference into the present patent application.

A subject of the invention is also a cosmetic or dermatological assembly comprising:

a) a container delimiting at least one compartment, the container being closed by a closing member; and
b) a composition placed inside the compartment, the composition being as defined above.

The invention is illustrated in greater detail by the non-limiting examples described below. The amounts are indicated as weight percentages.

| Composition (O/W emulsion) | Example 1 according to the invention | Example 2 according to the invention | Comparative Example 3 | Comparative Example 4 |
|---|---|---|---|---|
| PHASE A | | | | |
| Water | qs 100% | qs 100% | qs 100% | qs 100% |
| Hostacerin AMPS | 1% | 1% | — | — |
| Carbopol 980 | — | — | 0.5% | 0.5% |
| Preserving agent | 0.3% | 0.3% | 0.3% | 0.3% |
| PHASE B | | | | |
| Cyclohexasiloxane | 10% | 10% | 10% | 10% |
| Caprylic/capric triglycerides | 5% | 5% | 5% | 5% |
| Shea butter | 1% | 1% | 1% | 1% |
| PEG-20 methylglucose sesquistearate | 2.5% | 2.5% | 2.5% | 2.5% |
| Preserving agent | 0.25% | 0.25% | 0.25% | 0.25% |
| PHASE C | | | | |
| Triethanolamine | — | — | 0.25% | 0.25% |
| PHASE D | | | | |
| Polymethyl methacrylate(filler) | 2% | 2% | 2% | 2% |
| PHASE E | | | | |
| N-(2-Hydroxyethyl)urea | 7% | 14% | 7% | 14% |
| Viscosity (spindle 3) Measured 24 hours after preparation | 21 poises (2.1 Pa · s) | 24 poises (2.4 Pa · s) | 17 poises (1.7 Pa · s) | 14 poises (1.4 Pa · s) |

Alternatively, the container is made of non-thermoplastic material, especially glass or metal (or alloy).

The container may have rigid walls or deformable walls, especially in the form of a tube or a tubular bottle.

The container may comprise means for distributing or facilitating the distribution of the composition. By way of example, the container may have deformable walls so as to cause the composition to exit in response to a positive pressure inside the container, this positive pressure being caused by elastic (or non-elastic) squeezing of the walls of the container.

The container may consist or be comprised of a carton with a base delimiting at least one housing comprising the composition, and a lid, especially articulated on the base, and capable of at least partially covering the base. Such a carton is described, for example, in patent application WO 03/018423 or in patent FR 2 791 042.

The container may be equipped with a drainer arranged in the region of the aperture of the container. Such a drainer makes it possible to wipe the applicator and possibly the rod Procedure: The components of phase A and of phase B were heated separately. Phase A was poured into phase B and the phases were mixed until an emulsion was formed. For the gel comprising carbopol (Examples 3 and 4), the mixture was neutralized with phase C. The resulting mixture was cooled to 50° C. and phase D was added, while fully dispersing the filler. Phase E was then added and stirring was continued until the composition was completely homogenized.

This table shows that the O/W emulsions according to the invention have a satisfactory viscosity that does not change as the N-(2-hydroxyethyl)urea content is increased, whereas the comparative examples which comprise Carbopol 980, a carboxyvinyl polymer, have a lower viscosity, which, in addition, decreases linearly as the N-(2-hydroxyethyl)-urea content is increased.

The above written description of the invention provides a manner and process of making and using it such that any person skilled in this art is enabled to make and use the same, this enablement being provided in particular for the subject matter of the appended claims, which make up a part of the original description and including a composition, such as a cosmetic and/or dermatological composition, comprising, in an aqueous medium, (a) at least one compound of formula (I) below:

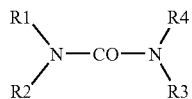

in which:
R1, R2, R3 and R4 represent, independently of each other, a hydrogen atom, a C1-C4 alkyl group or a C2-C6 hydroxyalkyl group possibly comprising from 1 to 5 hydroxyl groups, in which at least one of the radicals R1 to R4 represents a hydroxyalkyl group, and also the salts, solvates and isomers thereof, and (b) at least one polymer comprising at least one monomer comprising a sulfonic group.

As used above, the phrases "selected from the group consisting of," "chosen from," and the like include mixtures of the specified materials.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

Terms such as "contain(s)" and the like as used herein are open terms meaning 'including at least' unless otherwise specifically noted.

As used herein, where a certain polymer is noted as being "obtained from " or as "comprising", etc. one or more monomers (or monomer units) this description is of the finished polymer material itself and the repeating units therein that make up, in whole or part, this finished product. One of ordinary skill in the art understands that, speaking precisely, a polymer does not include individual, unreacted "monomers," but instead is made up of repeating units derived from reacted monomers. Thus, and for example, the phrase "at least one polymer comprising at least one monomer comprising a sulfonic group" refers to a finished polymer material itself and the repeating units therein that make up, in whole or part, this finished product.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

The invention claimed is:

1. A composition comprising, in an aqueous medium:
(a) at least one compound of formula (I) below:

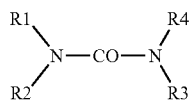

in which:
R1, R2, R3 and R4 represent, independently of each other, a hydrogen atom, a C1-C4 alkyl group, or a C2-C6 hydroxyalkyl group having from 1 to 5 hydroxyl groups, stereoisomers thereof, and salts and solvates thereof,
wherein at least one of the radicals R1 to R4 represents a hydroxyalkyl group, and
(b) at least one polymer comprising at least one 2-acrylamido-2-methylpropanesulfonic acid monomer.

2. The composition according to claim 1, comprising at least one compound of formula (I) wherein R1 denotes a C2-C6 hydroxyalkyl group and R2, R3 and R4 denote, independently of each other, a hydrogen atom or a C1-C4 alkyl group.

3. The composition according to claim 1, comprising at least one compound of formula (I) wherein R1 denotes a C2-C6 hydroxyalkyl group and R2, R3 and R4 denote a hydrogen atom.

4. The composition according to claim 3, wherein R1 denotes a C2-C6 hydroxyalkyl group comprising one hydroxyl group.

5. The composition according to claim 1, comprising at least one compound of formula (I) wherein R1 denotes a C2-C4 hydroxyalkyl group comprising one hydroxyl group and R2, R3 and R4 denote a hydrogen atom.

6. The composition according to claim 1, comprising at least one compound of formula (I) chosen from N-(2-hydroxyethyl)urea; N-(2-hydroxypropyl)urea; N-(3-hydroxypropyl)urea; N-(2,3-dihydroxypropyl)urea; N-(2,3,4,5,6-pentahydroxyhexyl)urea; N-methyl-N-(1,3,4,5,6-pentahydroxy-2-hexyl)urea; N-methyl-N'-(1-hydroxy-2-methyl-2-propyl)urea; N-(1-hydroxy-2-methyl-2-propyl)urea; N-(1,3-dihydroxy-2-propyl)urea; N-[tris(hydroxymethyl)methyl]urea; N-ethyl-N'-(2-hydroxyethyl)urea; N,N-bis(2-hydroxyethyl)urea; N,N'-bis(2-hydroxyethyl)urea; N,N-bis(2-hydroxypropyl)urea; N,N'-bis(2-hydroxypropyl)urea; N,N-bis(2-hydroxyethyl)-N'-propylurea; N,N-bis(2-hydroxypropyl)-N'-(2-hydroxyethyl)urea; N-tert-butyl-N'-(2-hydroxyethyl)-N'-(2-hydroxypropyl)urea; N-(1,3-dihydroxy-2-propyl)-N'-(2-hydroxyethyl)urea; N,N-bis(2-hydroxyethyl)-N',N'-dimethylurea; N,N,N'N'-tetrakis(2-hydroxyethyl)urea; and N'N'-bis(2-hydroxyethyl)-N',N'-bis(2-hydroxypropyl)urea.

7. The composition according to claim 1, comprising N-(2-hydroxyethyl)urea.

8. The composition according to claim 1, comprising at least one salt of a compound of formula (I), wherein the salts of the compounds of formula (I) are chosen from the salts of sulfuric acid, hydrochloric acid, hydrobromic acid, hydriodic acid, phosphoric acid, boric acid, propionic acid, acetic acid, terephthalic acid, citric acid and tartaric acid.

9. The composition according to claim 1, wherein the compound(s) of formula (I) is (are) present in an amount of 0.1% to 50% by weight relative to the total weight of the composition.

10. The composition according to claim 1, wherein the at least one polymer comprising at least one 2-acrylamido-2-methylpropanesulfonic acid monomer further comprises at least one monomer chosen from vinylsulfonic acid, styrenesulfonic acid, (meth)acrylamido($C_1$-$C_{22}$)alkylsulfonic acids, N-($C_1$-$C_{22}$)alkyl(meth)acrylamido($C_1$-$C_{22}$)alkylsulfonic acids, and the partially or totally neutralized forms thereof, and mixtures thereof.

11. The composition according to claim 1, wherein the at least one polymer comprising at least one 2-acrylamido-2-methylpropanesulfonic acid monomer is a crosslinked and neutralized 2-acrylamido-2-methylpropanesulfonic acid homopolymer.

12. The composition according to claim 1, wherein the at least one polymer comprising at least one 2-acrylamido-2-methylpropanesulfonic acid monomer is at least one amphiphilic homopolymer chosen from random amphiphilic polymers of 2-acrylamido-2-methylpropanesulfonic acid modified by reaction with a $C_6$-$C_{22}$ mono-n-alkylamine or di-n-alkylamine.

13. The composition according to claim 1, wherein the at least one polymer comprising at least one 2-acrylamido-2-methylpropanesulfonic acid monomer is at least one polymer selected from crosslinked anionic copolymers of acrylamide or methacrylamide and of 2-acrylamido-2-methylpropanesulfonic acid, copolymers of (meth)acrylic acid or of (meth)acrylate and of 2-acrylamido-2-methylpropanesulfonic acid, and copolymers of 2-acrylamido-2-methylpropanesulfonic acid and of vinylpyrrolidone or of vinylformamide.

14. The composition according to claim 1, wherein the at least one polymer comprising at least one 2-acrylamido-2-methylpropanesulfonic acid monomer is at least one hydrophobic modified polymer obtained from 2-acrylamido-2-methylpropanesulfonic acid and from at least one ethylenically unsaturated hydrophobic monomer comprising at least one group comprising from 6 to 50 carbon atoms.

15. The composition according to claim 14, wherein the ethylenically unsaturated hydrophobic monomer is chosen from the acrylates or acrylamides of formula (III) below:

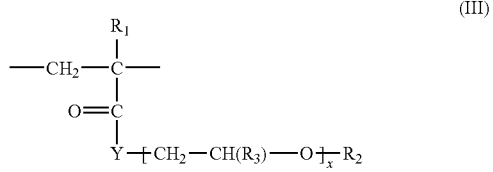

(III)

in which $R_1$ and $R_3$, which may be identical or different, denote a hydrogen atom or a linear or branched $C_1$-$C_6$ alkyl radical; Y denotes O or NH; $R_2$ denotes a hydrocarbon-based radical comprising from 6 to 50 carbon atoms; x denotes a number of moles of alkylene oxide and ranges from 0 to 100.

16. The composition according to claim 15, wherein the hydrocarbon-based radical $R_2$ is chosen from linear, branched or cyclic $C_6$-$C_{18}$ alkyl radicals; $C_6$-$C_{18}$ perfluoroalkyl radicals; the cholesteryl radical or a cholesterol ester; and aromatic polycyclic groups.

17. The composition according to claim 15, wherein the monomer of formula (III) comprises at least one alkylene oxide unit (x≧1).

18. The composition according to claim 14, wherein the hydrophobic modified polymer is chosen from:
crosslinked or non-crosslinked, neutralized or non-neutralized copolymers comprising from 15% to 60% by weight of AMPS units and from 40% to 85% by weight of ($C_8$-$C_{16}$)alkyl(meth)acrylamide units or of($C_8$-$C_{16}$) alkyl (meth)acrylate units, relative to the polymer;
terpolymers comprising from 10 mol % to 90 mol % of acrylamide units, from 0.1 mol % to 10 mol % of AMPS units and from 5 mol % to 80 mol % of n-($C_6$-$C_{18}$)alkyl-acrylamide units, relative to the polymer;
non-crosslinked copolymers of partially or totally neutralized AMPS and of n-dodecyl, n-hexadecyl or n-octadecyl methacrylate;
crosslinked or non-crosslinked copolymers of partially or totally neutralized AMPS and of n-dodecylmethacrylamide.

19. The composition according to claim 14, wherein the hydrophobic modified polymer is chosen from copolymers comprising 2-acrylamido-2-methylpropanesulfonic acid units of formula (II):

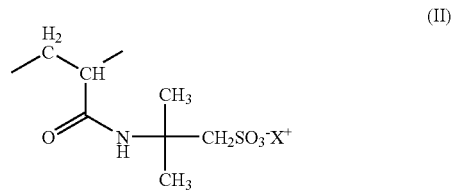

(II)

in which $X^+$ is a proton, an alkali metal cation, an alkaline-earth metal cation or an ammonium ion, and
(ii) of units of formula (IV) below:

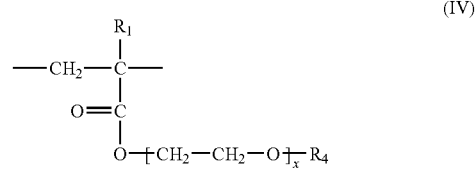

(IV)

in which x denotes an integer ranging from 3 to 100; $R_1$ is a hydrogen atom or a linear or branched $C_1$-$C_6$ alkyl radical and $R_4$ denotes a linear or branched alkyl radical comprising from 6 to 22 carbon atoms.

20. The composition according to claim 1, wherein the at least one polymer comprising at least one 2-acrylamido-2-methylpropanesulfonic acid monomer is present in an amount of from 0.01% to 20% by weight relative to the total weight of the composition.

21. The composition according to claim 1, wherein the composition comprises water in an amount of at least 30% by weight relative to the total weight of the composition.

22. The composition according to claim 1, further comprising at least one oily phase.

23. The composition according to claim 1, wherein the composition is a skin care product, a skin makeup product, an anti-sun product or a skin cleansing product.

24. A process for treating a keratin material, comprising applying a composition according to claim 1 to a keratin material.

25. A closed container containing therein the composition of claim 1.

* * * * *